United States Patent [19]

Blatt et al.

[11] Patent Number: 4,761,381

[45] Date of Patent: Aug. 2, 1988

[54] VOLUME METERING CAPILLARY GAP DEVICE FOR APPLYING A LIQUID SAMPLE ONTO A REACTIVE SURFACE

[75] Inventors: Joel M. Blatt, Granger; Robert Heiland, Goshen; James R. Morris, South Bend; Jerry Pugh, Elkhart; Frank W. Wogoman, South Bend, all of Ind.

[73] Assignee: Miles Inc., Elkhart, Ind.

[21] Appl. No.: 20,185

[22] Filed: Feb. 26, 1987

Related U.S. Application Data

[63] Continuation-in-part of Ser. No. 777,273, Sep. 18, 1985, abandoned.

[51] Int. Cl.[4] .................. G01N 21/78; G01N 33/52

[52] U.S. Cl. .................. 436/165; 356/246; 422/57; 422/58; 422/102; 436/166

[58] Field of Search .................. 422/55-58, 422/61, 72, 102; 436/165-166; 356/244, 246; 435/805, 810; 350/534-536

[56] References Cited

U.S. PATENT DOCUMENTS

| | | | |
|---|---|---|---|
| 3,690,836 | 9/1972 | Buissiere et al. | 422/102 X |
| 3,705,000 | 12/1972 | Guerra | 356/246 |
| 3,715,192 | 2/1973 | Wenz et al. | 422/56 |
| 3,876,377 | 4/1975 | Cinqualbre | 422/58 |
| 3,961,346 | 6/1976 | White | 356/246 X |
| 3,961,899 | 6/1976 | Trivedi et al. | 356/246 |
| 4,088,448 | 5/1978 | Lilja et al. | 422/58 X |
| 4,233,029 | 11/1980 | Columbus | 422/58 X |
| 4,260,687 | 4/1981 | Jacobson et al. | 422/61 |
| 4,310,399 | 1/1982 | Columbus | 422/58 X |
| 4,426,451 | 1/1984 | Columbus | 422/58 X |
| 4,647,430 | 3/1987 | Eweig | 422/58 |
| 4,690,801 | 9/1987 | Anderson | 422/102 |

*Primary Examiner*—Barry S. Richman
*Assistant Examiner*—Lyle Alfandary-Alexander
*Attorney, Agent, or Firm*—Roger N. Coe

[57] ABSTRACT

A method for controlling a liquid volume flowing onto a reactive surface which includes a sample application port, two systems of capillary channels, a reaction chamber, and an overflow chamber. The liquid sample to be analyzed is applied to the sample application port which gives the liquid entry to a capillary channel leading to the reaction chamber which contains a material capable of detecting the component of interest in the liquid. When the reaction chamber is filled, the remaining liquid will flow through another capillary channel to an overflow chamber. The capillary channel leading to the overflow chamber is controlled so that liquid cannot flow back into the reaction chamber.

36 Claims, 6 Drawing Sheets

FIG. 1
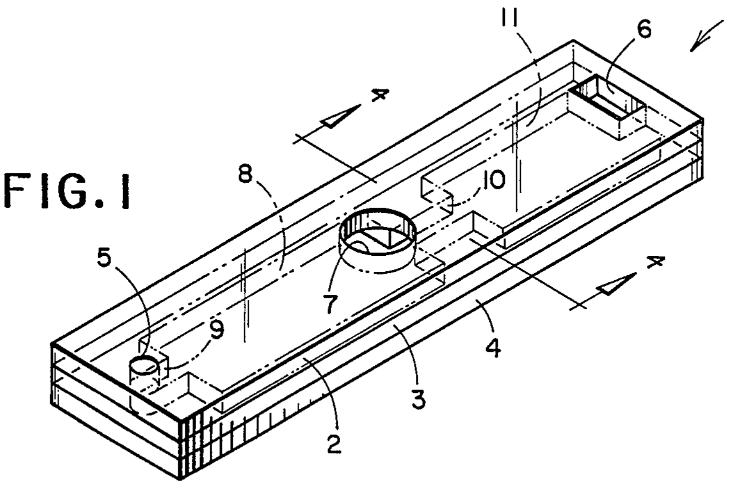
FIG. 2
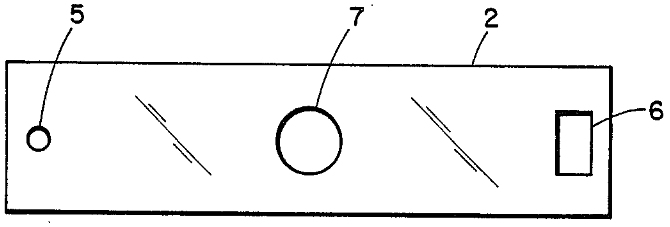
FIG. 3
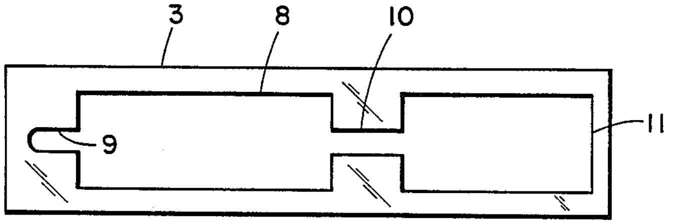
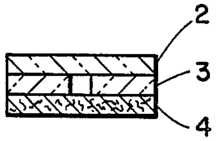
FIG. 4
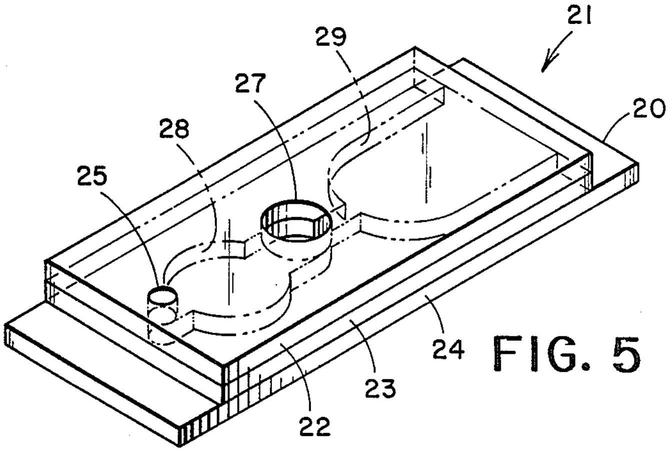
FIG. 5

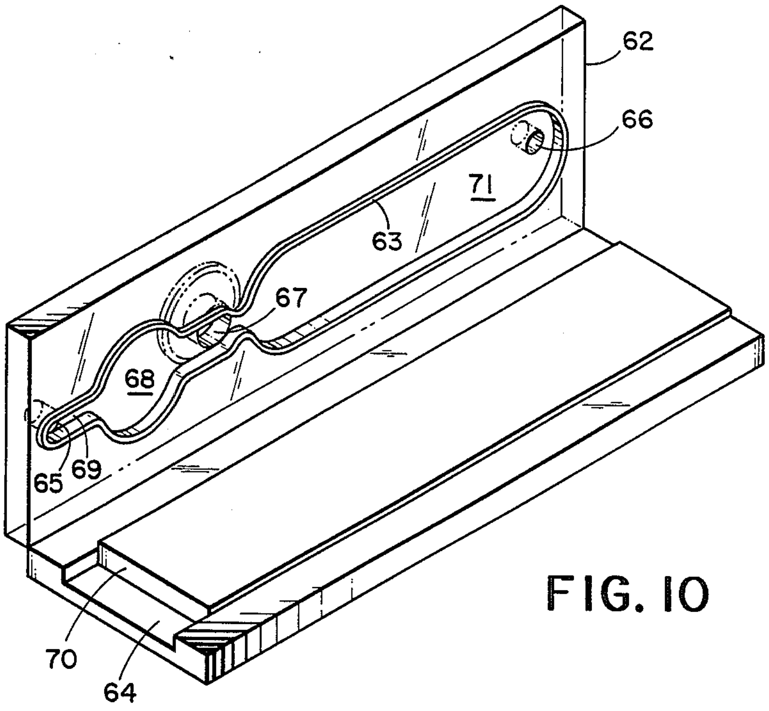
FIG. 10
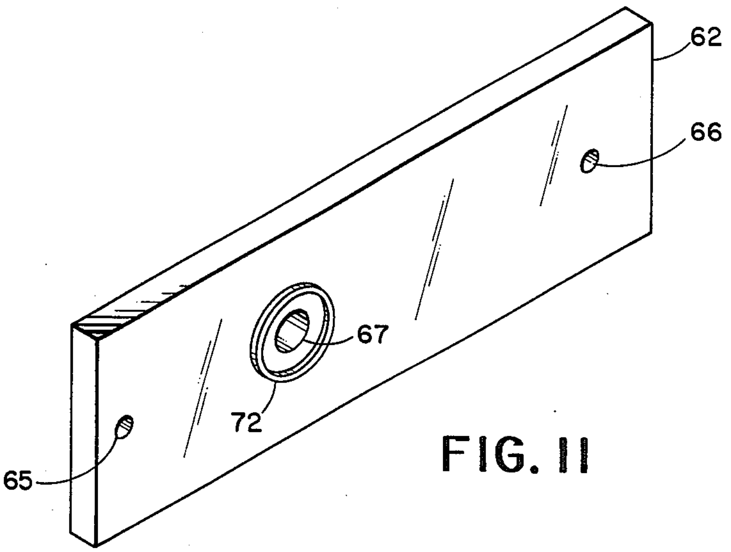
FIG. 11
FIG. 12
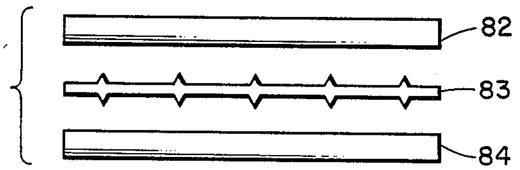

DOSE - RESPONSE FOR GLUCOSE
FILM EFFECT OF FORMAT DESIGN

VOLUME METERING CAPILLARY GAP DEVICE FOR APPLYING A LIQUID SAMPLE ONTO A REACTIVE SURFACE

RELATED APPLICATION

This is a continuation-in-part of copending application Ser. No. 777,273, filed Sept. 18, 1985, now abandoned.

FIELD OF THE INVENTION

The present invention relates to a device and method for distribution of a liquid sample in controlled and predetermined flow patterns and, more particularly, to a device and method that permits rapid and uniform distribution of a defined volume of a liquid test specimen onto a reactive surface which enables visual or other sensing means to ascertain the presence of a sought after component in the liquid sample and/or the amount of said component.

DESCRIPTION OF THE PRIOR ART

Analytical elements have been known for many years. The chemical analysis of liquids such as water, foodstuffs, such as milk, as well as biological fluids such as blood and urine are often desirable or necessary for the health and welfare of any population. Many different designs of test elements to facilitate analyses have been developed in the past. Some are suitable for liquid analysis which require the addition of a liquid reagent for a substance under analysis termed an "analyte" which reagent upon contacting a liquid sample containing the analyte effects formation of a colored material or other detectable change in response to the presence of the analyte. Other systems depend on a dry system such as pH papers and the like, where the paper or other highly absorbent carrier is impregnated with a material which is chemically reactive or responsive in contact with the liquid containing the analyte and generates a color or other type of change. Depending upon the selection of responsive material, the change is usually qualitative or at best semi-quantitative. For diagnostic chemical analysis wherein the testing of biological fluids such as blood, plasma, urine and the like are utilized, it is preferable to produce highly quantitative results rapidly and conveniently. Also, it is desirable to precisely control and monitor the amount of liquid specimen that is subjected to the test. This is important especially in tests which involve machine reading of test substrates where it is necessary that a calibrated amount of the test specimen is exposed to the test substrate so that the proper reaction will take place and that any interference with optical detection or other detection of color changes is avoided.

A variety of devices and methods have been developed for transporting liquid in a controlled and predetermined flow pattern. Many of such items have been concerned with uncontrolled and undirected capillary flow of the liquid across surfaces. Some problems that have been encountered with uncontrolled flow include formation of trapped air pockets and incomplete wetting of certain portions of the surface. Air pockets create problems when the test device is examined through a microscope or other automatic methods because the examination of the liquid and/or the wetted surfaces results in different test data being collected. The examinations and automated systems are based on a presumption of the presence of the liquid in the scanning area and therefore the absence of the liquid in the relevant scanning area will throw off the value of the reading and will give an unreliable result. The problem of air pockets is a common occurrence particularly when dealing with configurations which have sharp corners and synthetic resin surfaces which are generally hydrophobic.

A variety of different types of liquid transport devices have been developed in the prior art including that shown in Columbus, U.S. Pat. No. 4,233,029, which describes a device containing a means for directing capillary flow along predetermined paths by use of grooves in the opposed surfaces of a capillary chamber.

Another configuration for the transport of a liquid test specimen is shown in Columbus, U.S. Pat. No. 4,254,083, which provides for an exterior drop receiving surface containing a particular opening configuration which is intended to facilitate the centering of the drop.

Buissiere et al., U.S. Pat. No. 3,690,836, describe a device consisting of a capillary space between two plastic sheets which are sealed in a continous perimeter and which enclose an uncompressed absorbent material which fills the capillary space. At least one opening at the top sheet provides for access to the reaction chamber.

A liquid transport device which provides for diversion of capillary flow into a second zone is shown in Columbus, U.S. Pat. No. 4,473,457. The device has two pathways for flow of the specimen and permits the introduction of two different specimens through two apertures. The two liquids then will flow towards and into a common area. The configuration of the structure of Columbus permits potentiometric determinations to be made. See also Columbus, U.S. Pat. No. 4,302,313, which shows a device suitable for potentionmetric analysis of liquid ions. Special grooved surfaces under the member 36 are said to control capillary flow.

Another device is shown by Columbus, U.S. Pat. No. 4,271,119, which has a downstream diverting aperture in a wall member of a first capillary zone which provides capillary flow into a second capillary zone extending from that wall member.

Columbus, U.S. Pat. No. 4,323,536, discloses a multianalyte test device. Liquid flow control means are included such that liquid is confined to a plurality of flow paths.

SUMMARY OF THE INVENTION

The present invention pertains to a means for volume metering of liquid samples onto a reactive surface in a capillary gap device of novel configuration. The device provides for a rapid and uniform distribution of a predetermined volume of a liquid test specimen onto a reactive surface for the determination of a particular component or components that may or may not be present in the liquid test specimen. The volume of sample applied to the surface is limited to that amount which resides within a sample capillary gap or sample reading chamber. Excess sample is wicked into an overflow capillary chamber by a proportioning channel which modifies the rate of flow thereby permitting the device to accommodate excess volume above the minimum required for the sample reading chamber without requiring any measuring, blotting, wipe-off or rinsing.

Major problems associated with dry reagent films and papers are solved by the present invention; namely, application of a uniformly distributed sample onto a reactive surface and control of the sample volume.

The aforementioned advantages permit one to choose a sample volume appropriate to the chemistry and reactivity of the reactive material by varying the thickness of the capillary gap and hence the total volume entrained by the sample reading chamber of the device.

Excess fluid beyond the capacity of the capillary overflow chamber may be absorbed by filter paper or other absorbent medium attached to the device adjacent to or directly over a suitable opening of the overflow chamber.

Other features and advantages of the present invention will become apparent from the following detailed description taken in conjunction with the drawings.

BRIEF DESCRIPTION OF THE DRAWINGS

FIG. 1 is a perspective view of one embodiment of the capillary gap device of the present invention;

FIG. 2 is a top view of the top layer of one embodiment of the capillary gap device of the present invention showing the openings or ports formed therein;

FIG. 3 is a top view of the spacer layer of one embodiment of the capillary gap device of the present invention showing the chamber formed therein;

FIG. 4 is an end view of the capillary gap device taken along lines 4—4 in FIG. 1;

FIG. 5 is a perspective view of another embodiment of the present invention;

FIG. 10 is an exploded view of an alternative arrangement of the present invention;

FIG. 11 is a perspective view of the upper layer shown in FIG. 10;

FIG. 12 is a schematic side view of another embodiment of the invention showing a particular configuration for a spacer layer;

Figure 6:
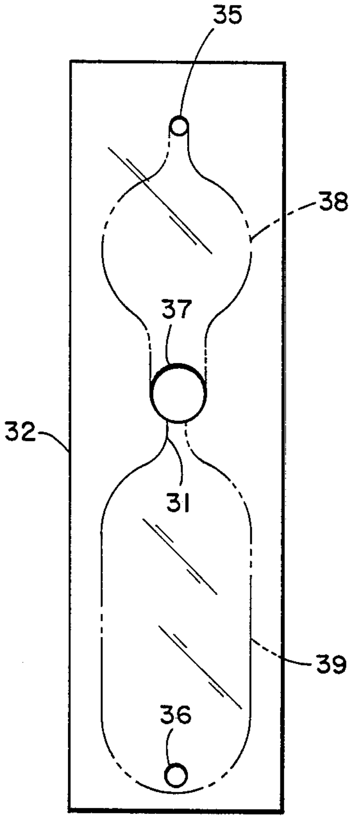
FIG. 6 is a top view of an alternative arrangement of the present invention.

Major problems associated with dry reagent films and papers are solved by the device of the invention. It is difficult utilizing prior art materials to obtain an application of an uniformly distributed sample over a finite surface area of a test surface. In many instances, the sample will not travel into the sample chamber under proper conditions, too much sample is in contact with the sample chamber or not enough of the liquid is in contact therewith. The present invention permits close and carefully monitored control of the sample volume so that only a previously determined calibrated amount of liquid to be analyzed will be in contact with the test surface. Therefore, these advantages permit one to choose a sample volume that is appropriate to the particular test that is being carried out taking into consideration the nature of the fluid that is being tested and the nature of the reagent film. The present invention can be fabricated in various different dimensions and therefore the thickness of the capillary gap can be varied as desired. Hence, the capillary gap devices can be made in various sizes depending upon the total volume of the sample that is desired to be entrained of the sample. This will depend upon the particular means chosen for reading the results; i.e., either automatic or visual means. The device of the present invention provides a means for dealing with the problem of excess sample so that any excess liquid does not interfere with obtaining a proper reading. Thus, in accordance with the invention, excess fluid flows into an overflow chamber through an overflow proportioning channel and, if necessary, out an overflow port or opening. If desired, some sort of absorbing material can be either attached to the device or adjacent thereto so as to absorb the excess liquid.

It is important to note that the present invention is not simply a fluid transport or spreading device but instead is a volume metering device which is designed to accommodate a range of sample volumes from a minimum of about 5 to 10 micro liters up to about 100 to 200 micro liters without washing or wiping off the excess liquid.

It is therefore an important feature of the present invention to provide a fluid metering device in a capillary gap structure containing a sample chamber of a defined volume.

It is a further feature of the present invention to provide a capillary gap device which has a capillary lock for air release and prevention of backflow into the sample application port.

A further feature of the present invention is to provide for proportioned flow of the sample fluid into a capillary overflow chamber which accommodates the liquid volume beyond the minimum required to fill the sample chamber. The volume of the sample chamber can be varied to accommodate excess sample as well when this is compatible with the chemistry of the reagent film that is chosen.

A further feature of the present invention is to provide for complete removal of sample fluid from the sample application port by capillary action. Thus, no washing or wiping is required nor does any excess sample fluid remain exposed in the aperture. In operation in accordance with the invention, any residual sample which remains in the sample application port would be drawn into the overflow chamber and the sample application port is thereby evacuated. Any excess overflow beyond the capacity of the capillary overflow chamber can be taken care of by utilizing an absorbent pad as an optional feature of the invention.

A still further feature of the present invention is a capillary gap device wherein no exchange can occur between liquid in the sample chamber and liquid in the overflow chamber due to the creation of an air gap in the overflow proportioning channel. This can enchance the end point chemistries which are carried out in the sample chamber depending upon the particular nature of the reactive material.

DETAILED DESCRIPTION OF INVENTION

Described in further detail, the device of this invention features a capillary transport for biological liquids particularly whole blood which can be visually inspected or subjected to an automated system for sample reading. The device can be utilized with any liquid in drop form wherein a certain amount of the liquid is to be carried through an opening port from an exterior surface or source to transport means for transporting the liquid to the reactive surface or test substrate. The device of the present invention features the metering of the fluid into a capillary gap containing a sample chamber of a defined volume.

The device of the present invention as represented by the embodiment of the invention illustrated in FIG. 1 includes a capillary device 1, of generally rectangular geometry, having a major axis and a minor axis and including a top layer 2, a spacer layer 3, and a bottom layer 4. The bottom layer comprises reagent detection means. The top layer, which may or may not be clear and transparent, is illustrated as being a transparent plastic material and has formed in the top surface thereof, an air relief port 5, an overflow port 6 and a sample application or sample introduction port 7. It will be understood, however, that the openings or ports can be located on the end or bottom of the device provided the ports do not interfere with the operation of the device.

The spacer layer 3 which defines the internal capillary gap or chamber generally coincides in dimension with the top layer 2 and bottom layer 4 and has formed therein a sample chamber 8 with a capillary lock area 9 coincident with the space below the air relief port 5 in the top layer 2. While the capillary gap can vary, it generally ranges from 0.007 to 0.08 cm. Also formed in the spacer layer is an overflow proportioning channel 10 connecting the sample chamber 8 to the overflow chamber 11. The overflow chamber 11 is located beneath and connects with the overflow port 6 in the top layer 2. It will be noted that the sample chamber 8 and the overflow chamber 11 are of relatively large area while the proportioning channel 10 connecting the two chambers is of relatively narrow dimensions.

The reagent layer 4 can comprise a mono or multilayer reagent material or a substrate of any conventional type as described in further detail hereafter.

The clear top layer 2 can be cut or stamped from a suitable material, such as Trycite, a polystyrene material. Other plastic substances are polyolefins, polyamides, polyester and the like as will be apparent to those skilled in the art. Any suitable material can be used provided it is inert to the test specimens and sufficiently strong and stable.

The spacer layer can be formed of any suitable material such as a thermoplastic material which, upon heating, can be utilized to adhere the top layer 2 to the reagent bottom layer 4. Any suitable dimensionally stable thermoplastic material can be used for this purpose such as polyamides, polyethylene, polypropylene, PVC, copolymers thereof and the like. Alternatively, a separate adhesive composition can be interposed between the several layers in a sufficient amount to adhere all layers together in a secure and permanent fashion. Such adhesive substances are known in the art and any suitable one can be used provided it does not react with any test specimens.

It will be understood that any suitable way of joining the layers together can be used. Among other ways of assembling the various layers are welding the layers (e.g. ultrasonically), snapping the layers together and wrapping tape around the outside edges of the layers.

The dimensions of the capillary gap device can vary widely but it has been found that a particularly useful dimension is a ratio of about 3 to 1 length vs. width; that is, 2.5 to 7.5 cm (about 1 to 3 inches) in length by 0.8 to 2.4 cm (⅓ to 1 inch) in width. A particularly useful configuration is 3.7 cm (1.4 inches) in length by 1 cm (0.4 inch) in width. The thickness of the test device can also vary and generally is 0.05 to 0.25 cm (about 0.02 to 0.1 inch). Typically, the three layers can include (1) a 0.02 cm (0.008 inch) thick plastic such as polystyrene cover, (2) a plastic and adhesive spacer layer which can be approximately 0.02 cm (0.006 inch) thick with approximately shaped cutouts for fluid containment and (3) a bottom reactive layer which consists of a gelatin based coating on a polyethyleneterephthalate film base; e.g. 0.02 cm (0.008 inch) thick.

In FIG. 2, there is shown the embodiment of the top layer shown in FIG. 1 showing the air relief port 5, the overflow port 6 and the sample application port 7. The dimensions of these openings can vary as well as their geometry. Most conveniently, they are circular openings because they can easily be drilled or punched out in a thin sheet. However, FIG. 2 shows that the overflow port is rectangular, a shape that can be punched out with a suitable die. The air relief port 5 can be relatively small, say, about 0.08 cm (0.03 inch) in diameter located on the center major axis of top layer 2 and located a small distance from the end, for example 0.06 cm (0.025 inch), with the center of the circle being at about 0.1 cm (0.04 inch) from the end. Thus, if the width of the top cover is 1 cm (0.4 inch) the center line of air relief port 5 will be at 0.5 cm (0.2 inch) in from the long edge. The rectangular overflow port 6 is located a small distance (e.g. 0.1 cm or 0.04 inch) from the end opposite that where air relief port 5 is located. The dimensions of the overflow port can vary, but for example 0.3 by 0.5 cm (0.1 by 0.2 inch) has been found to be suitable. The overflow port, like the air relief port, is normally centered on the major axis of the test device.

The sample application port 7 can also be circular in shape and typically is larger in open area than the air relief port 5. For example, the diameter of the sample application port is customarily 3 to 4 times greater than the diameter of the air relief port 5. Thus, based on the above discussed dimensions, a suitable dimension for the application port is 0.3 cm (0.1 inch) in diameter. The location of sample application port 7 can be in the center of the device although it need not necessarily be centered. The important thing is that it be positioned so as to be in communication with the sample chamber 8 and contiguous to the overflow proportioning channel 10.

FIG. 3 shows a top view of the spacer chamber layer 3 with the sample chamber 8 and the overflow chamber 11 connected by the overflow proportioning channel 10 and also shows the capillary lock 9. In this embodiment of the invention, the several different areas in spacer layer 3 are all located symmetrically with respect to the major axis of the device. The capillary lock 9 and the overflow proportioning channel are relatively narrow compared to sample chamber 8 and overflow chamber 11. Sample chamber 8 and overflow chamber 11 are of greater volume than the channel 10. For example, the lock and channel can be 0.08 cm (0.03 inch) wide while the width of the chambers is 0.8 cm (0.03 inch), i.e. about 10 to 1, although the exact size and relative size can vary. In general, ratios between 2 to 1 and 50 to 1 can be employed. The spacer chamber can also be formed of a thermoplastic resin that will function as adhesive as well to thereby enable fusion of the three layers together to bond them into a unit. Alternatively, a conventional adhesive can be used to bond the several layers together. In still a further variation, ultrasonic or laser means can be used to achieve proper bonding. In a yet further variation, a mechanical clamp can be used to maintain the layers together.

FIG. 4 is a cross-sectional end view of the device showing the top, spacer and bottom layers. The bottom layer 4 is the reagent containing layer and can be a reagent impregnated fibrous layer or a gelatin coated layer. Any one of a wide variety of reagent layers or substrates, including powders, can be used in accordance with the invention. Many conventional reagent systems are available and the specific choice of which reagent selected will depend upon the tests to be carried out.

FIG. 5 is a perspective view of a different embodiment of capillary gap device 21 of the invention composed of three layers; i.e., a transparent top or cover layer 22, a spacer layer 23 and a reagent film layer 24. In this embodiment, reagent film layer 24 has an extended portion 20 upon which an absorbent material to absorb the overflow of liquid from the overflow chamber 29 can be placed. In this variation, there is no overflow port on the top layer. Instead, the overflow flows out of the end of the device directly into extended portion 20 of the reagent layer 24. Further, in this embodiment, the chamber walls are contoured in curved shape which avoid sharp corners.

FIG. 6 shows a top view of still a further embodiment of the invention with the air relief port 35, overflow port 36 and sample application port 37. The chamber for the sample 38 and for the overflow 39 are contoured, as may be seen when viewed through the transparent top 32, so that sharp corners are avoided. An overflow proportioning chamber 31 is also shown.

Figure 7:
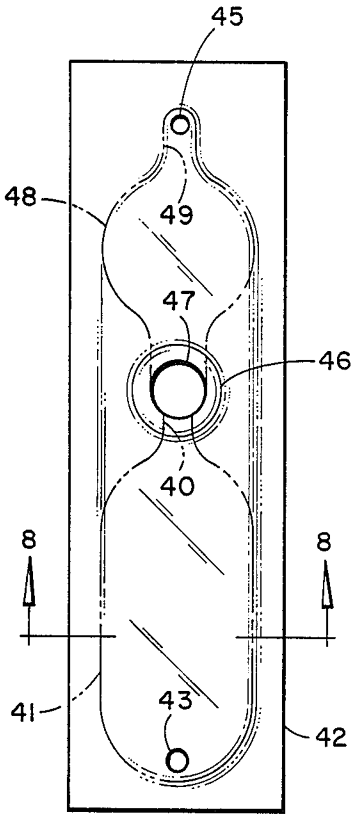
FIG. 7 is a top view of another embodiment of the invention.

FIG. 7 shows another embodiment of the invention and is a top view of the capillary gap device. The top layer 42 and a reagent layer 44 (FIG. 8) are joined together by an adhesive (not shown). No spacer layer is present in this embodiment. The top sheet has shaped therein the air relief port 45, capillary lock 49, sample chamber 48, sample application port 47, proportioning channel 40, overflow chamber 41 and sample relief port 43. In addition, it has a raised ring 46 formed around the sample application port 47 to enable centering of the liquid drop of sample, to assist in the guidance of the liquid sample drop into the sample application port 47 and to aid in removing sample from the applicator, e.g., a finger.

Figure 8:
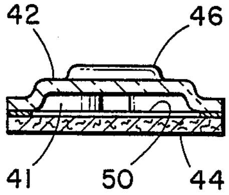
FIG. 8 is an end view of the embodiment shown in FIG. 7 taken along lines 8—8.

FIG. 8 shows the embodiment of FIG. 7 in cross-section. In this embodiment, the top layer is molded to form therein upwardly extended chambers 48 (not shown) and 41 while the reagent layer is flat. Between the upper layer 42 and the reagent layer 44 an adhesive material 50 can be used to bond the two layers together. The ring 46 is shown surrounding the sample port 47 (not shown). It is understood that the reagent material can also have an adhesive layer around the perimeter thereof to enable bonding or heat sealing to the top layer without the use of a separate adhesive material.

Figure 9:
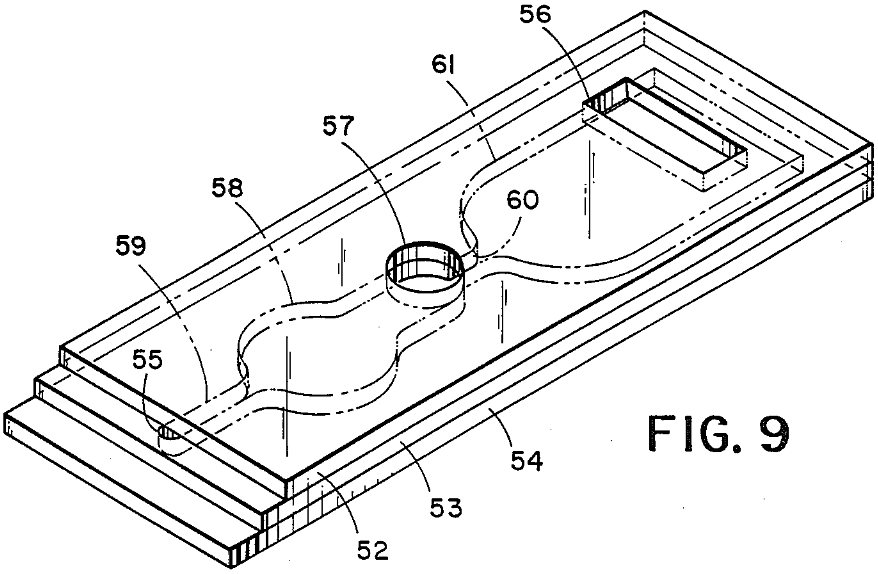
FIG. 9 is a perspective view of another embodiment of the invention.

A further embodiment of the invention is shown in FIG. 9 in perspective view and consists of the transparent cover layer 52 having formed therein the sample application port 57 and overflow port 56. The spacer layer 53 which has the chambers formed therein can be formed of a suitable material and has the capillary lock 59, sample chamber 58, overflow metering proportioning channel 60 and overflow chamber 61 formed therein. By staggering the layers, the terminal end of the capillary lock 59 can extend out beyond the end of the cover layer 52 and thereby provides the air release port 55. The reagent layer 54 can be any suitable reagent material.

A further embodiment of the invention is shown in FIG. 10 which shows an exploded view of a capillary gap device of the present invention. The device is formed of a top surface layer 62 which is transparent and which has the air relief port 65, the overflow port 66 and the sample introduction port 67 formed therein. The top layer 62 has formed in the underside thereof the overflow chamber 71, sample application chamber 68 and the capillary lock area 69. It can also have a sealing ridge or a slightly thicker portion 63 outlining the edges of the chambers and channels. The bottom layer is provided with a channel or groove 64 for retaining reagent 70. The bottom layer is made of a clear transparent plastic or other material to permit viewing through the clear surface. The longitudinal groove for the reagent is slightly shallower than the film thickness. The bottom layer has raised longitudinal edge surfaces which can be formed of a heat sealable plastic or can have an adhesive formed thereon which permits the welding or adhesion of the bottom layer to the top layer. A suitable adhesive can also be applied between the top surface and the bottom layer. Preferably, the top layer can be formed of a thermoplastic material which when subjected to heating or ultrasonic welding can result in fusion of the top surface together with the bottom surface.

FIG. 11 shows the upper surface of the top layer 62 depicted in FIG. 10. In this embodiment, the sample application port 67 is provided with a raised ring 72 which aids in centering the drop of sample for introduction into the device.

FIG. 12 is a schematic side view of the three elements used to form a capillary device of the invention. The top 82 and bottom, or reagent, layer 84 are as described above. The spacer layer 83 is formed of a plastic material that is heat deformable and is punched out or molded to form channels and chambers. The top and bottom surfaces of layer 83 has dimples, pyramids or projections formed thereon to provide for good welding and bonding together when the layers are united.

Figure 13:
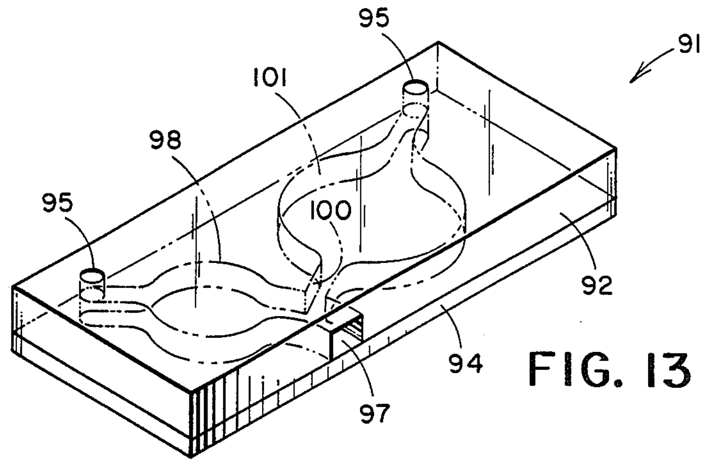
FIG. 13 is a perspective view of another embodiment of the capillary gap device of the present invention.

Another embodiment of the present invention is illustrated in FIG. 13 and includes a capillary device 91, of generally rectangular geometry which is formed of a top layer 92 and a bottom reagent layer 94. In this embodiment of the invention, there is no separate spacer layer. The sample chamber 98, overflow chamber 101 overflow metering channel 100, and all other openings, ports and channels are directly formed in the top layer 92. These openings, passageways and chambers can be formed in the top layer 92 by drilling, cutting out, or any other means of formation that may be convenient. In this embodiment of the invention, the sample entry port 97 is located on the edge or side of the capillary device 91 instead of on the top surface of top layer 92. In this embodiment which has the end or edge filling sample port, there is less likely to be a problem caused by blockage or entrappment of a bubble of air. Further, wiping action to remove excess sample may not be necessary since the device can be placed directly against a drop of blood or fluid and will fill upon contact with only so much of the fluid being taken up by the capillary device as is necessary to fill the sample chamber, with any excess being drawn into the overflow chamber.

As is the case with other embodiments, the top layer can be clear and transparent, or translucent to facilitate observation. It could also be opaque. As illustrated in the drawing, it is shown as being a transparent plastic material. Any convenient and known plastic or other synthetic materials can be used for this purpose such as polystyrene, polyolefins, polyamides, polyesters and the like. Further, as the case with other embodiments, the dimensions of the capillary gap device are generally similar but can vary as convenient or as desired.

The reagent layer 94 can be formed of a mono- or multilayer reagent material or substrate as will be apparent.

The reagent layer can be conveniently secured to the top layer by any suitable adhesive material (not shown) which may be separately applied in a sufficient amount to adhere both layers together in a secure, permanent fashion. Alternatively, depending upon the composition of top layer 92 and reagent layer 94, they can be thermally fused together or fused by laser means or any other suitable means as will be apparent to those skilled in the art.

Figure 14:
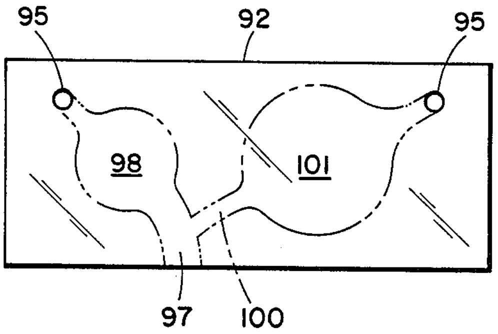
FIG. 14 is a top view of the top layer of the embodiment of the invention shown in FIG. 13.

FIG. 14 shows the top layer 92 of the device in FIG. 13 and shows two air relief ports 5, the sample entry side port 97, the sample chamber 98, overflow chamber 101 and overflow metering or proportionating channel 100. The dimensions of these openings, passageways and chambers can vary as well as their specific geometry. In general, depending upon how the top layer is formed, the side walls will be generally vertical but the contours can be circular or curve-like. The dimensions of the air relief port, thickness of the top layer between the top surface and the chamber and other dimensions are generally the same as previously given in connection with other embodiments of the invention. However, it should be noted that these dimensions can change and be varied as will be found to be convenient.

The sample application port which is formed on the side in this embodiment of the invention is typically square or rectangular in shape simply for purposes of convenience in stamping out or cutting out these openings. If more convenient, it can be made to be circular, oval or any other desired shape. The location of the side entry port can be placed at any suitable location along the side or edge of the capillary device and need not be centered thereon. Naturally, it is important that the side entry port be in communication with sample entry chamber and also contiguous to the overflow proportioning channel 100 which leads to the overflow chamber 101.

Figure 15:
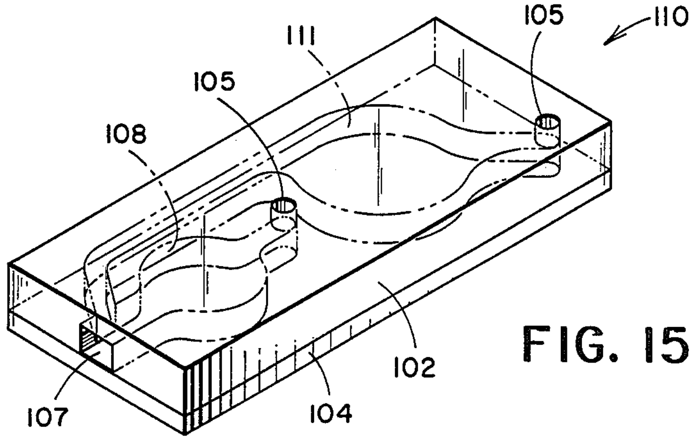
FIG. 15 is a perspective view of another embodiment of the capillary gap device of the present invention.

FIG. 15 is a perspective view of a further embodiment of the invention wherein the sample entry port 107 is located on the edge of the capillary gap device 110; that is, on the side which is coincident with the minor axis of the generally rectangularly shaped capillary device. In this embodiment, the capillary gap device is formed of two layers, a top layer 102 and a reagent film bottom layer 104. There is no separate spacer layer in this embodiment of the device, although it should be understood that the device having this configuration with the side or edge sample entry port can also be made in accordance with the embodiment shown in FIG. 1; that is, with a top layer, a spacer layer and a reagent film or bottom layer.

FIG. 15 shows that the device contains a sample chamber 108, an overflow chamber 111, an overflow metering channel 112 connecting the sample chamber to the overflow chamber. Each of the chambers is equipped with an air vent 105. In this embodiment, the various chambers and channels can also be cut, stamped or molded into the top layer 102 in accordance with any convenient technique or method. The configuration of the sample entry port, shown as generally square-like in FIG. 15 can be rectangular, round, elliptical or any other desired shape. The top layer can be made of any suitable transparent, trauslucent or opaque layer as previously mentioned with regard to other embodiments of the invention. Likewise, the reagent layer 104 can be a mono- or multilayer reagent containing layer as heretofore described. The top layer 102 and the reagent film layer 104 can be bonded together by using adhesive means, by heating or by any other suitable method.

Figure 16:
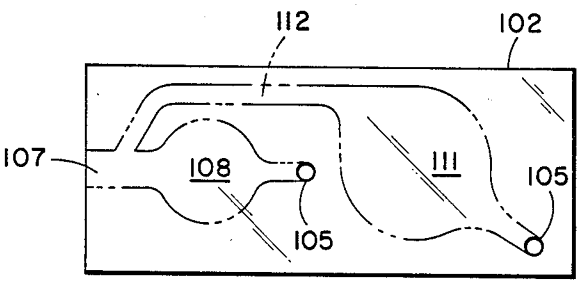
FIG. 16 is a top view of the top layer of the embodiment of the invention shown in FIG. 15.

FIG. 16 shows a top view of the top layer 102 of FIG. 15. The top layer has formed therein the air vents 105, the sample chamber 108 and the overflow chamber 111. In this embodiment of the invention, there is a relatively long overflow metering channel 112 which is connected to the sample chamber near the sample port opening 107. The embodiment shown in FIG. 16 is merely illustrative of various configurations, shapes and formations that can be formed in a top layer in accordance with this embodiment of the invention.

In the variations of the invention shown in FIGS. 13 to 16, there is no overflow port shown as this is not usually necessary when having a side entry port. When using the side or sample entry port, excess fluid is not usually a problem and therefore generally there is no need for the overflow port. Of course, it should be understood that if more convenient, an overflow port can be easily formed directly into the top layer as will be apparent from the foregoing description. As will be apparent from FIGS. 13 to 16, the chamber walls of the various chambers and passageways are contoured generally in a curve-shape to avoid sharp corners.

Figure 17:
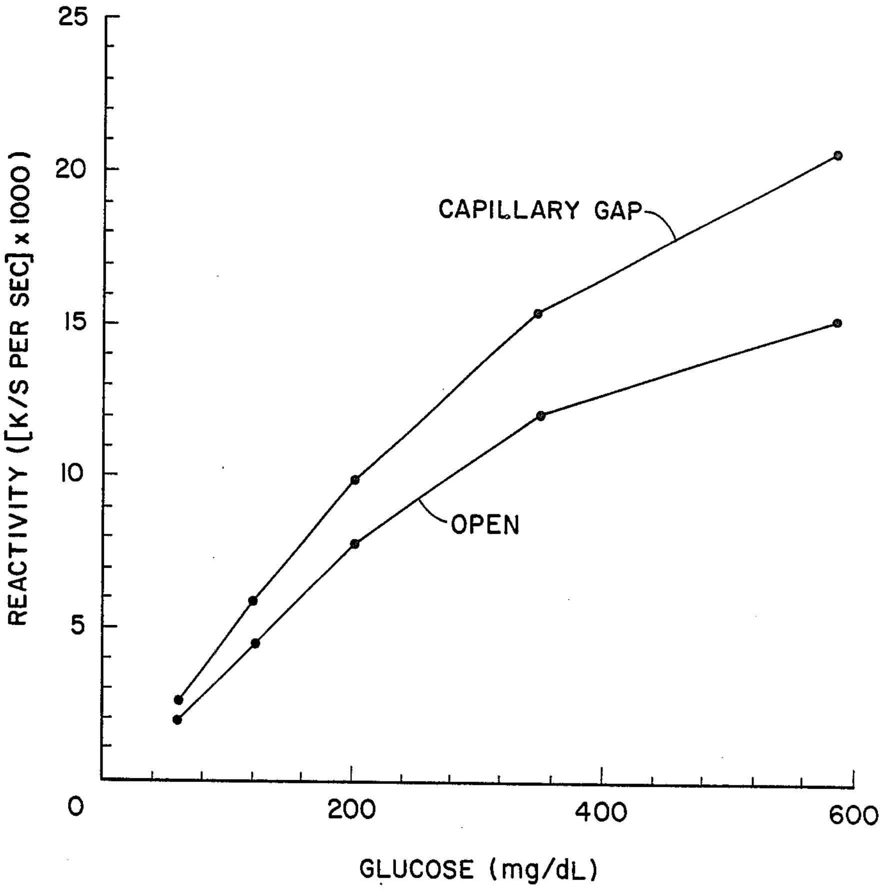
FIG. 17 is a graph of the reactivity per second and describes the effect of format design on the dose response film curve for a glucose sensitive film.
Figure 18:
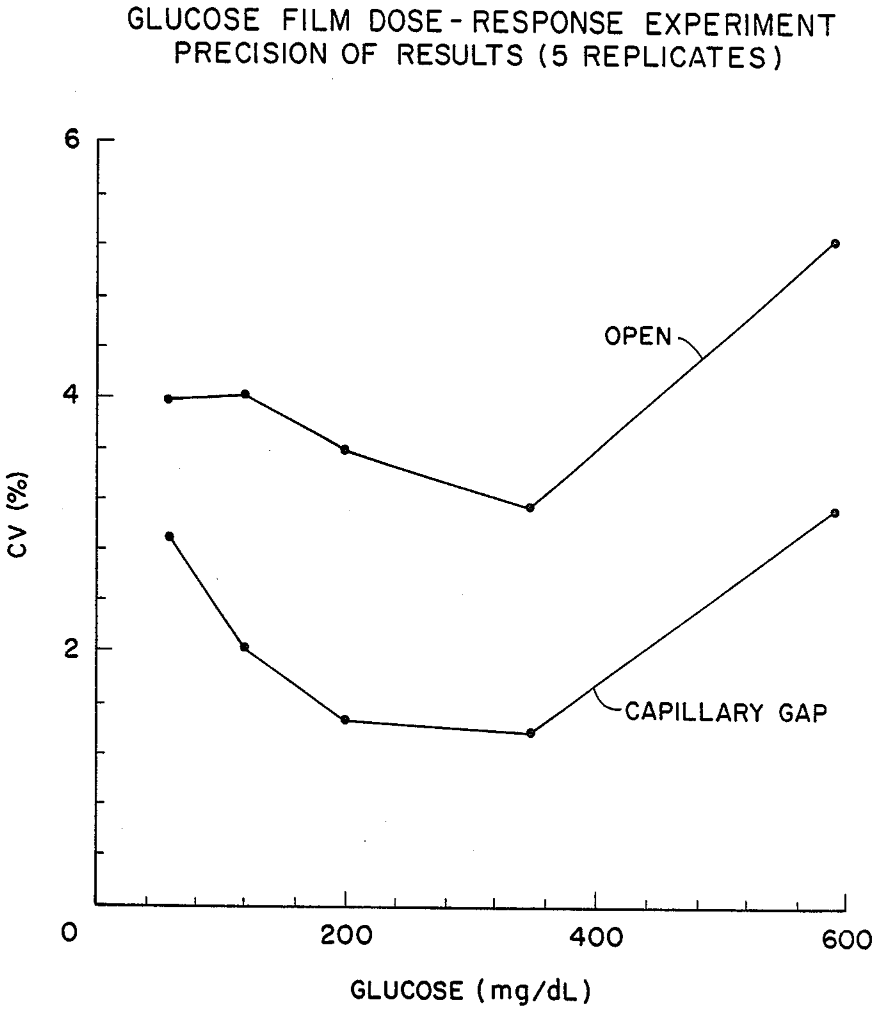
FIG. 18 shows a comparison of test precision for an open and a capillary gap format device.

FIG. 17 shows the results of a dose response experiment where the glucose film in the capillary gap format is compared to a currently used open format; that is, where an open drop of blood is deposited on a glucose film confined to a small area by the hole in a plastic covering layer. The reactivity of the film in the capillary gap format is significantly higher than that in the open format. One explanation may be evaporative cooling of the exposed sample in the open format which lowers the sample temperature by about 2.5° C. Assay precision can be improved by a factor of as much as two in the capillary gap format as evidenced by lower coefficients of variation (CV) at each glucose concentration, as shown in FIG. 18.

In accordance with the invention as shown, for example, in FIG. 1, a capillary gap device 1 can be constructed which has a multilayer reagent film as the bottom layer 4 wherein the film base is the lower most layer, a layer of double sided adhesive plastic film as the spacer layer 3 and a top covering layer 2 of plastic. The shape of the sample chamber 8 and the overflow chamber 11 and overflow proportioning channel 10 and capillary lock channel 9 is determined by cutting out voids in the adhesive layer and access to these chambers is provided by the openings 5, 6 and 7 in the plastic cover layer 2.

As an alternative, the adhesive pattern in accordance with the desired configuration of chambers and channels can be printed or screened onto the inner surface of the covering layer in whatever thicknesses required.

It should be noted that the rectangular chamber shapes as shown in FIG. 1 can be formed by conventional tooling for punching out the adhesive film. A still further preferred embodiment is shown in FIG. 5 which shows rounded contours. Rounded contours are usually achieved by molding techniques.

A further alternative method of manufacture resides in forming the capillary channels and chambers directly in the plastic covering layer. This is shown in FIG. 8. This embodiment of the invention permits complex, smoothly contoured shapes to be formed in an appropriate thermoplastic material by applying heat in combination with vacuum or pressure and an appropriately shaped mold or dye. Adhesive means can then be employed to attach the formed plastic covering layer to the reagent film without significantly adding further to the thickness of the device. It should be noted that other device geometries employing the same general principles can be adapted to capillary gap devices.

In the embodiments shown in FIGS. 13 to 16, there is no separate spacer layer and the chambers and passageways are cut or shaped into the top layer which is of suitable thickness to accommodate these areas.

In operation, a sample of blood or fluid containing the desired analyte such as glucose, for example, is applied to the sample application port, either to the top, edge or end depending upon the embodiment. Typically, the device can handle a minimum sample volume of about 20 micro liters. Any excess volume remains in the sample application port for a brief period of time until it is removed by capillary action into the overflow chamber. This usually occurs within about 20 seconds, at which time the sample application port is completely evacuated of any specimen. Initial filling of the sample chamber requires less than a few seconds, typically about 2 seconds, and it is limited only by the rate at which the sample is applied to the sample application port.

In a further embodiment of the invention shown in FIG. 12, the capillary gap device is formed of a three layer construction. The top layer 82 is a transparent plastic such as polystyrene. The spacer layer 83 is formed of a thermoplastic material and contains the internal geometrical configuration of channels and chambers (not shown). Also, the upper and lower surfaces of layer 83 are formed with dimples, projections and/or pyramid shaped protrusions to provide energy directors for welding which can pierce the gelatin layer of the reagent film bottom layer 84. Typically, the bottom layer 84 can be formed of a reagent film such as a gelatin coated layer where the gelatin faces the top surface. When formed into a composite and welded together by means such as by ultrasonic welding, the spacer layer 83, which is formed of a thermoplastic material fusible under the conditions utilized in the ultrasonic welding operation fuses to the top layer 82 and bottom layer 84 to provide a uniform and secure seal between the several members. In this way, a large sheet of material can be formed and then cut by ultrasonic or laser welding into the desired sizes. Alternatively, the devices can be welded and cut by ultrasonic or laser means at the same time.

As explained above, the main purpose of the device of the invention is to provide metering of a defined sample volume to a reactive surface or path without requiring any measurement, washing or wiping of sample. In the device shown herein, excess sample liquid is drawn into the overflow chamber at a rate determined by the size of the proportioning channel. Furthermore, in the device of this invention, the fluid connection between the sample chamber and the overflow chamber is broken once the overflow chamber has removed excess sample fluid. The capillary lock serves to prevent backflow. The top and bottom inner surfaces of the device should be made of such materials that the wetting angles are similar. One manner of achieving this is to coat one or all surfaces with surface active agent.

Any reagent can be used for purposes of the invention provided the reagent contains at least one material that is interactive or responsive in the presence of an analyte positive liquid present in the specimen to be tested. In various instances, the interactive material can be responsive to an analyte or a precursor or a reaction product of an analyte to effect the production of a change within the element by virtue of the reactive material. Thus, the reagent layer is permeable to at least one component present in the sample and is preferably of a substantially uniform permeability to those substances which are tested for in the test specimen. The term "permeable" is used herein indicates the ability of a substance or the layer to be penetrated effectively by a material carried in the test liquid. Uniform permeability of a layer refers to permeability such that when a homogeneous liquid is provided uniformly to a surface of the layer, identical measurements of the concentration of such liquid within the layer can be made through different regions of the surface of the layer permitting substantially the same results, within about 10% to be obtained for each measurement. Because of the uniform permeability, undesirable concentration gradients can be avoided in the reagent layer. Such reagent layers are well known in the art and any suitable one can be used for purposes of the invention.

One or more surface active agents can be utilized to coat the interior of the chambers in the device so as to permit and facilitate liquid transport of the specimen into the sample chamber and the excess liquid overflow compartment. A broad variety of ionic and nonionic surface active agents can be used for this purpose. For example, the well known ionic surface active agents such as alkali metal and alkyl sulfates, wherein the alkyl group has more than 8 carbon atoms, such as sodium dodecyl sulfate, can be utilized. Nonionic surface active agents such as the many examples set forth in McCutcheon's "Detergents and Emulsifyers" 1974, North American Edition by the Allured Publishing Corporation can be used.

Analytical elements of the present invention can be adapted for use in carrying out a wide variety of chemical analyses, not only in the field of clinical chemistry but in chemical research and in chemical process control laboratories. Theoretically, the invention can be used under low gravity conditions, including those conditions found in outer space. The invention is well suited for use in clinical testing of body fluids, such as blood, blood serum and urine, since in this work a large number of repetitive tests are frequently conducted and test results are often needed a very short time after the sample is taken. In the field of blood analysis, for example, the multilayer element can be adapted for use in carrying out quantitative analyses for many of the blood components which are routinely measured. Thus, for example, the element can be readily adapted for use in the analysis of such blood components as urea nitrogen, chloride, glucose and uric acid, as well as many other components by appropriate choice of test reagents or other interactive materials. In analyzing blood with an analytical element of this invention, the blood cells may first be separated from the serum, by such means as centrifuging, and the serum applied to the element. However, it is not necessary to make such separation, especially if reflective spectrophotometric analysis techniques are used to quantify or otherwise analyze the reaction product formed in the element as whole blood can be applied directly to the element and the blood cells filtered out through the action of a filtering layer. The presence of these cells on the element will not interfere with spectophotometric analysis if it is carried out by reflection techniques.

Reagent layers in the devices of the invention can be permeable or porous to samples obtained from a metering or spreading layer or to reaction products thereof. A multilayer reagent layer can include a metering or spreading layer. As used herein, the term "permeability" includes permeability arising from porosity, ability to swell or any other characteristic. Reagent layers can also include a matrix in which an interactive material is distributed, i.e., dissolved or dispersed. The choice of a matrix material is, of course, variable and dependent on the intended use of the element. Desirable matrix materials can include hydrophilic materials such a hydrophilic colloids, preferably in the form of a water-swellable gel. Useful hydrophilic materials include both naturally occurring substances like gelatin, gelatin derivatives, hydrophilic cellulose derivatives, polysaccharides such as dextran, gum arabic, agarose and the like, and also synthetic substances such as water-soluble polyvinyl compounds like polyvinyl alcohol and polyvinyl pyrrolidone, acrylamide polymers, etc. Organophilic materials such as cellulose esters and the like can also be useful, and the choice of materials in any instance will reflect the use for which a particular element is intended.

To enhance permeability of the reagent layer if not porous, it is often useful to use a matrix material that is swellable in the solvent or dispersion medium or liquid under analysis. The choice of a reagent layer matrix in any given instance may also depend in part on its optical or other properties that could affect radiometric detection. The reagent layer should be non-interfering with respect to any intended result detection procedure. Also, it may be necessary to select material that is compatible with the application of an adjacent layer, such as by coating means, during preparation of the element. As an example, where the formation of discrete layers is desired and the intended analysis will be of aqueous liquids, it may be appropriate to select an essentially water soluble matrix for the reagent layer and essentially organosoluble or organodispersible ingredients for an adjacent layer, such as a spreading layer. In such manner, mutual solvent action is minimized and a clearly delineated layer structure can be formed. In many cases, to facilitate the formation within the spreading layer of such apparent concentrational uniformity as is discussed herein, it may be desirable to have the reagent layer of lower permeability than is the spreading layer itself. Relative permeability can be determined by well-known techniques.

In various embodiments of the present elements, the interactive material in the reagent layer interacts with the analyte material to which the element is responsive. In other embodiments, the interactive material can interact with a precursor or a product of an analyte, as appropriate in view of the analysis mechanism of choice. The term "interactive" is meant herein to refer to chemical reactivity such as reactivity by addition, protonation, decomposition, etc., activity as in the formation of an enzyme-substrate complex, activity as is produced as a result of enzymatic action as well as any other form or composition of chemical or physical interaction able to produce or promote within the element, such as in the reagent layer, the formation of a radiometrically detectable change, i.e., one that is detectable by suitable measurement of light or other electromagnetic radiation.

The distribution of interactive material can be obtained by dissolving or dispersing it in the matrix material. Although uniform distributions are often preferred, they may not be necessary if the interactive material is, for example, an enzyme. Reagents or other interactive materials soluble in the liquid under analysis can advantageously be immobilized in the reagent layer, particularly when the reagent layer is porous.

The particular interactive materials that can be distributed within a reagent layer will depend on the analysis of choice. In the case of glucose analysis, a ferricyanide compound can be used. Glucose reacts with ferricyanide and the reaction causes a decrease in the yellow color characteristic of ferricyanide. In testing for uric acid, as in blood of serum, a mixture of copper sulfate and neocuproine can be distributed in the reagent layer matrix. Uric acid causes reduction of cupric copper to cuprous copper that can complex with the neocuproine to form a colored material that is proportional in density to the concentration of uric acid in the analyzed liquid. In the case of many analyses, enzymes such as oxidase materials like glucose oxidase can desirably be included as interactive materials within a reagent layer of an element intended for the analysis of an analyte that is a substrate for such enzyme. As an example, an oxidative enzyme can be incorporated into a reagent layer together with peroxidase or a peroxidative material and a chromogen material or composition that, upon oxidation in the presence of peroxidase (or another substance having peroxidative activity) and the hydrogen peroxide formed upon interaction of an oxidase and its substrate, provides a dye or other detectable species. An interactive material that, upon appropriate interaction, provides directly a detectable change in the element is also termed an indicator. A plurality of materials, including at least one interactive material, that act together to provide a detectable change in the element is collectively termed an indicator composition.

Chromogenic materials or compositions that contain an oxidizable moiety and can provide a detectable species include certain dye providing materials or compositions. In one aspect, a dye can be provided by a compound, that when oxidized, can couple with itself or with its reduced form to provide a dye. Such autocoupling compounds include a variety of hydroxylated compounds such as orthoaminophenols, alkoxynaphthols, 4-amino-5 pyrazolones, cresols, pyrogallol, guaiacol, orcinol, catechol phloroglucinol, p,p-dihydroxydiphenyl, gallic acid, pyrocatechoic acid, salicyclic acid, etc. Compounds of this type are well known and described in the literature, such as in *The Theory of the*

*Photoqraphic Process,* Mees and James Ed. (1966), especially at Chapter 17. In another aspect, the detectable species can be provided by oxidation of a leuco dye to provide the corresponding dyestuff form. Representative leuco dyes include such compounds as leucomalachite green and leucophenolphthalein. In yet another aspect, the detectable species can be provided by dye providing compositions that include an oxidizable compound capable of undergoing oxidative condensation with couplers such as those containing phenolic groups or activated methylene groups, together with such a coupler. Representative such oxidizable compounds include such compounds as benzidene and its homologs, p-phenylenediamines, p-aminophenols, 4-aminoantipyrine, etc. A wide range of such couplers, including a number of autocoupling compounds, is described in the literature.

Alternatively, some materials or compositions contain a reducible moiety that can provide a radiometrically detectable compound. This compound may be either formed or destroyed by the reductive process. Examples of the former type of chemistry may be found in the direct radiometric measurement, usually at a wavelength of 340 nanometers, of reduced nicotinamide adenine dinucleotide (reduced NAD) as may be formed by the reaction of glucose with glucose dehydrogenase and NAD, as well as in the further reaction of reduced NAD with diaphorase and any one of a variety of tetrazolium compounds and subsequent radiometric detection of the resulting formazan. A specific example of such a tetrazolium is iodonitrotetrazolium chloride (INT) which, upon reduction, produces a red colored formazan. 2,6-Dichlorophenolindophenol is an example of a compound whose color is destroyed upon reduction.

The test element layer can be optionally transparent so that it can be read from the bottom as desired. This layer can have a variety of binder compositions, for example, gelatin, cellulose acetate butyrate, polyvinylalcohol, agarose and the like, the degree of hydrophilicity of which depends on the material selected. Gelatin is generally suitable to act as a layer when testing blood since it acts as a wetting agent to provide for an unique liquid flow through the capillary zone.

Additional layers can also be arranged to provide for a variety of chemistries or function and to provide a function in its own layer or in combination with another reagent layer. Thus, a plurality of layers can be utilized. Filtering, registration or mordanting functions can be provided for by additional layers. Prior art is replete with examples of multiple layers such as is found in U.S. Pat. Nos. 4,042,335 and 4,050,898, for example.

As used herein, the terms "reagent" and "reagent layer" mean a material that is capable of interaction with an analyte, a precursor of an analyte, a decomposition product of an analyte or an intermediate. For example, one of the reagents can be a radiometrically detectable species which is mobilized by the analyte from a radiometrically opaque portion or layer of the element to a radiometrically transparent portion or layer such as a registration layer.

Interaction between the reagents of the reagent composition and the analyte is therefore meant to refer to chemical reaction, catalytic activity as in the formation of an enzyme substrate complex or any other form of a chemical or physical interaction including physical displacement that can produce ultimately a radiometrically detectable signal in the element.

The present invention enables one to monitor the filling of the sample chamber by use of a white or light colored reagent film and an opaque or black cover sheet and then observing the appearance of sample through the air release port. Superior temperature control characteristics are achieved by the present invention relative to noncapillary as well as most other capillary devices because virtually no fluid sample remains exposed to the atmosphere. This means that the invention almost completely eliminates evaporative cooling effects. Once a device is filled with a sample, it is insensitive to orientation. No air filled spaces remain in the sample chamber and the sample cannot leak out. Initial filling should be performed on a reasonably level surface to ensure an even distribution of the sample. The analyte sensitive surface contained in the device is protected from environmentally caused damage and degradation since it remains enclosed except for the apertures in the top covering layer.

Further modifications and variations of the invention will be apparent from the foregoing and are intended to be encompassed by the claims appended hereto.

What is claimed is:

1. A flow metering capillary device for controlled fluid flow of test liquid comprising oppositely disposed top and bottom surface layers defining therebetween a capillary zone of intended liquid transport of a test liquid, said top and bottom surface layers being spaced apart at a distance no greater than which will maintain a capillary flow of said test liquid therebetween and wherein said capillary zone is divided into a sample test chamber containing interactive material capable of reaction with a component of said test liquid to provide a detectable response and an overflow chamber for excess test liquid, an overflow proportioning channel located between said sample test chamber and said overflow chamber which functions to permit overflow of test liquid from the sample test chamber to the overflow chamber and as a capillary lock to break connection between test liquid in the sample chamber and test liquid in the overflow chamber and which prevents backflow of the test liquid from the overflow chamber to the sample chamber, and means defining a sample application port for introduction of said test liquid into said capillary zone, said sample application port being in communication with said sample test chamber and contiguous to said overflow proportioning channel.

2. The device as set forth in claim 1, wherein said distance is between about 0.007 and about 0.08 centimeter.

3. The device as set forth in claim 1, wherein the top surface layer is transparent.

4. The device as set forth in claim 1, wherein the interactive material is a reagent impregnated responsive layer.

5. The device as set forth in claim 1, further comprising an adhesive layer interposed between said surface layers for sealing said surface layers together.

6. The device as set forth in claim 1, wherein said channel and said chambers are formed in the surface layers.

7. The device as set forth in claim 1, which said chambers are of substantially rectangular shape.

8. The device as set forth in claim 1, wherein the chambers are of a contoured configuration.

9. The device as set forth in claim 1, which additionally has present an absorbent wicking layer between said surface layers.

10. The device as set forth in claim 1, wherein the interactive material is a multiple reagent layer.

11. The device as set forth in claim 1, wherein a surface of the capillary zone is coated with a surface active agent.

12. The device as set forth in claim 1, wherein said sample application port is located at a side of said device.

13. The device as set forth in claim 1, wherein said sample application port is located at an end of said device.

14. The device as set forth in claim 1, wherein said sample test chamber and said overflow chamber are of relatively larger dimensional area and said channel connecting said chambers is of relatively smaller dimensional area, said channel being adjacent the sample application port.

15. The device as set forth in claim 1, wherein said sample application port comprises a sample entry port located at a side of said device, said port being a relatively narrow passageway connected to a sample test chamber of relatively larger area, said overflow chamber being connected to the relatively narrow passageway by an overflow metering channel.

16. The device of claim 1 which includes means for removing excess test liquid from said overflow chamber.

17. The device as set forth in claim 16, wherein said top surface layer has a means defining relief port for venting air from said sample test chamber and said means for removing excess test liquid comprises a means defining an overflow port connected to said overflow chamber for removing excess test liquid.

18. The device as set forth in claim 1, wherein the device is rectangular in shape having a major axis and a minor axis.

19. The device as set forth in claim 18, wherein the dimensions of the device are about 3.7 cm long by 1 cm wide.

20. The device as set forth in claim 1, wherein the sample application port has a circular ring around it which rises above an upper surface of the port defining means.

21. The device as set forth in claim 20, wherein the thickness of the device is 0.05 to 0.25 cm.

22. A flow metering capillary device for controlled fluid flow comprising a top surface layer, a bottom reagent interactive layer and a spacer layer positioned therebetween and defining a capillary zone of intended liquid transport of a dimension no greater than that which will maintain a capillary flow of liquid introduced into said zone, and wherein said capillary zone is divided into a sample test chamber containing interactive material capable of reacting with a component of said liquid to provide a detectable response and an overflow chamber for excess liquid, an overflow proportioning channel located between said sample test chamber and said overflow chamber which functions to permit overflow of liquid from the sample test chamber to the overflow chamber and as a capillary lock to break connection between liquid in the sample test chamber and liquid in the overflow chamber and which prevents backflow of the liquid from the overflow chamber to the sample test chamber, and means defining a sample application port for introduction of liquid into said capillary zone, said sample application port being in communication with said sample test chamber and contiguous to said overflow proportioning channel.

23. The device as set forth in claim 22, wherein said dimensions between about 0.007 and about 0.08 centimeter.

24. The device as set forth in claim 22, wherein the test chamber includes means defining an air relief vent opening.

25. The device as set forth in claim 22, further comprising an adhesive layer being formed on the underside of the top surface layer positioned in sealing relation to the spacer layer.

26. The device as set forth in claim 22, wherein the chambers are of substantially rectangular shape.

27. The device as set forth in claim 22, wherein the chambers are of a contoured configuration.

28. The device as set forth in claim 22, which additionally has present an absorbent wicking layer between the top and bottom layers.

29. The device as set forth in claim 22, wherein the interactive layer is a multiple reagent layer.

30. The device as set forth in claim 22, wherein the dimensions of the device are 3.7 cm long by 1 cm wide.

31. The device as set forth in claim 22, wherein the sample application port has a circular ring around it which rises above the surface of the port defining means.

32. The device as set forth in claim 22, wherein the thickness of the device is 0.05 to 0.3 cm.

33. The device as set forth in claim 22, wherein the surface of the top surface layer facing the capillary zone is coated with a surface active agent.

34. The device as set forth in claim 22, wherein the top surface layer is transparent.

35. The device as set forth in claim 22, wherein said spacer layer is a thermoplastic layer which bonds said top surface layer and interactive layer together.

36. A method for introducing a liquid into a test device comprising the steps of supplying a liquid to an application port of said test device which directs the fluid to a capillary channel that further directs said liquid into a reaction chamber containing interactive material capable of reacting with a component of said liquid to provide a detectable response, directing remaining fluid in excess of the volume of said reaction chamber into a second capillary channel arranged to direct said remaining liquid into an overflow chamber that functions to prevent said liquid back-flow from said overflow chamber into said reaction chamber, said capillary channels being sized to maintain a capillary flow of said liquid and said sample application port being in communication with said sample chamber and contiguous to said second capillary channel.

* * * * *